US010463078B2

United States Patent
Davis et al.

(10) Patent No.: US 10,463,078 B2
(45) Date of Patent: Nov. 5, 2019

(54) AEROSOL DELIVERY DEVICE WITH CONDENSING AND NON-CONDENSING VAPORIZATION

(71) Applicant: RAI Strategic Holdings, Inc., Winston-Salem, NC (US)

(72) Inventors: Michael F. Davis, Clemmons, NC (US); James Rogers, Winston-Salem, NC (US); Percy Philips, Pfafftown, NC (US); Ercilia Hernandez Garcia, Clayton, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 510 days.

(21) Appl. No.: 15/205,775

(22) Filed: Jul. 8, 2016

(65) Prior Publication Data

US 2018/0007967 A1    Jan. 11, 2018

(51) Int. Cl.
| | | |
|---|---|---|
| *A24F 47/00* | (2006.01) | |
| *A61M 11/00* | (2006.01) | |
| *A61M 15/00* | (2006.01) | |
| *A61M 15/06* | (2006.01) | |

(Continued)

(52) U.S. Cl.
CPC ......... *A24F 47/008* (2013.01); *A61M 11/005* (2013.01); *A61M 11/042* (2014.02); *A61M 15/0085* (2013.01); *A61M 15/06* (2013.01); *A61M 2016/0039* (2013.01); *A61M 2205/8206* (2013.01)

(58) Field of Classification Search
None
See application file for complete search history.

(56) References Cited

U.S. PATENT DOCUMENTS

| | | |
|---|---|---|
| 1,771,366 A | 7/1930 | Wyss et al. |
| 2,057,353 A | 10/1936 | Whittemore, Jr. |
| 2,104,266 A | 1/1938 | McCormick |

(Continued)

FOREIGN PATENT DOCUMENTS

| | | |
|---|---|---|
| AU | 276250 | 7/1965 |
| CA | 2 641 869 | 5/2010 |

(Continued)

OTHER PUBLICATIONS

Partial Search Report dated Oct. 10, 2017 in corresponding International application No. PCT/IB2017/054018 filed Jul. 3, 2017.

(Continued)

*Primary Examiner* — Thor S Campbell
(74) *Attorney, Agent, or Firm* — Womble Bond Dickinson (US) LLP

(57) ABSTRACT

An aerosol delivery device having condensing and non-condensing vaporization functionality is provided. The aerosol delivery device may comprise at least one housing, and a first element and second element contained within the at least one housing. The first and second element may be configured to activate and vaporize components of an aerosol precursor composition, and thereby form respectively a condensing vapor and non-condensing vapor. In response to a flow of air through at least a portion of the at least one housing, the condensing vapor or non-condensing vapor may be combinable with the air to form an aerosol.

16 Claims, 5 Drawing Sheets

(51) Int. Cl.
*A61M 11/04* (2006.01)
*A61M 16/00* (2006.01)

(56) References Cited

U.S. PATENT DOCUMENTS

| | | | |
|---|---|---|---|
| 3,200,819 A | 8/1965 | Gilbert | |
| 4,284,089 A | 8/1981 | Ray | |
| 4,303,083 A | 12/1981 | Burruss, Jr. | |
| 4,735,217 A | 4/1988 | Gerth et al. | |
| 4,848,374 A | 7/1989 | Chard et al. | |
| 4,907,606 A | 3/1990 | Lilja et al. | |
| 4,922,901 A | 5/1990 | Brooks et al. | |
| 4,945,931 A | 8/1990 | Gori | |
| 4,947,874 A | 8/1990 | Brooks et al. | |
| 4,947,875 A | 8/1990 | Brooks et al. | |
| 4,986,286 A | 1/1991 | Roberts et al. | |
| 5,019,122 A | 5/1991 | Clearman et al. | |
| 5,042,510 A | 8/1991 | Curtiss et al. | |
| 5,060,671 A | 10/1991 | Counts et al. | |
| 5,093,894 A | 3/1992 | Deevi et al. | |
| 5,144,962 A | 9/1992 | Counts et al. | |
| 5,249,586 A | 10/1993 | Morgan et al. | |
| 5,261,424 A | 11/1993 | Sprinkel, Jr. | |
| 5,322,075 A | 6/1994 | Deevi et al. | |
| 5,353,813 A | 10/1994 | Deevi et al. | |
| 5,369,723 A | 11/1994 | Counts et al. | |
| 5,372,148 A | 12/1994 | McCafferty et al. | |
| 5,388,574 A | 2/1995 | Ingebrethsen et al. | |
| 5,408,574 A | 4/1995 | Deevi et al. | |
| 5,468,936 A | 11/1995 | Deevi et al. | |
| 5,498,850 A | 3/1996 | Das | |
| 5,515,842 A | 5/1996 | Ramseyer et al. | |
| 5,530,225 A | 6/1996 | Hajaligol | |
| 5,564,442 A | 10/1996 | MacDonald et al. | |
| 5,649,554 A | 7/1997 | Sprinkel et al. | |
| 5,666,977 A | 9/1997 | Higgins et al. | |
| 5,687,746 A | 11/1997 | Rose et al. | |
| 5,726,421 A | 3/1998 | Fleischhauer et al. | |
| 5,727,571 A | 3/1998 | Meiring et al. | |
| 5,743,251 A | 4/1998 | Howell et al. | |
| 5,799,663 A | 9/1998 | Gross et al. | |
| 5,819,756 A | 10/1998 | Mielordt | |
| 5,865,185 A | 2/1999 | Collins et al. | |
| 5,865,186 A | 2/1999 | Volsey, II | |
| 5,878,752 A | 3/1999 | Adams et al. | |
| 5,894,841 A | 4/1999 | Voges | |
| 5,934,289 A | 8/1999 | Watkins et al. | |
| 5,954,979 A | 9/1999 | Counts et al. | |
| 5,967,148 A | 10/1999 | Harris et al. | |
| 6,040,560 A | 3/2000 | Fleischhauer et al. | |
| 6,053,176 A | 4/2000 | Adams et al. | |
| 6,089,857 A | 7/2000 | Matsuura et al. | |
| 6,095,153 A | 8/2000 | Kessler et al. | |
| 6,125,853 A | 10/2000 | Susa et al. | |
| 6,155,268 A | 12/2000 | Takeuchi | |
| 6,158,431 A | 12/2000 | Poole et al. | |
| 6,164,287 A | 12/2000 | White | |
| 6,196,218 B1 | 3/2001 | Voges | |
| 6,196,219 B1 | 3/2001 | Hess et al. | |
| 6,598,607 B2 | 7/2003 | Adiga et al. | |
| 6,601,776 B1 | 8/2003 | Oljaca et al. | |
| 6,615,840 B1 | 9/2003 | Fournier et al. | |
| 6,688,313 B2 | 2/2004 | Wrenn et al. | |
| 6,772,756 B2 | 8/2004 | Shayan | |
| 6,803,545 B2 | 10/2004 | Blake et al. | |
| 6,854,461 B2 | 2/2005 | Nichols | |
| 6,854,470 B1 | 2/2005 | Pu | |
| 7,117,867 B2 | 10/2006 | Cox et al. | |
| 7,293,565 B2 | 11/2007 | Griffin et al. | |
| 7,513,253 B2 | 4/2009 | Kobayashi et al. | |
| 7,775,459 B2 | 8/2010 | Martens, III et al. | |
| 7,832,410 B2 * | 11/2010 | Hon | A24F 47/008 131/273 |
| 7,845,359 B2 | 12/2010 | Montaser | |
| 7,896,006 B2 | 3/2011 | Hamano et al. | |
| 8,127,772 B2 | 3/2012 | Montaser | |
| 8,314,591 B2 | 11/2012 | Terry et al. | |
| 8,365,742 B2 | 2/2013 | Hon | |
| 8,402,976 B2 | 3/2013 | Fernando et al. | |
| 8,499,766 B1 | 8/2013 | Newton | |
| 8,528,569 B1 | 9/2013 | Newton | |
| 8,550,069 B2 | 10/2013 | Alelov | |
| 8,851,081 B2 | 10/2014 | Fernando et al. | |
| 2002/0146242 A1 | 10/2002 | Vieira | |
| 2003/0226837 A1 | 12/2003 | Blake et al. | |
| 2004/0118401 A1 | 6/2004 | Smith et al. | |
| 2004/0129280 A1 | 7/2004 | Woodson et al. | |
| 2004/0200488 A1 | 10/2004 | Felter et al. | |
| 2004/0226568 A1 | 11/2004 | Takeuchi et al. | |
| 2005/0016550 A1* | 1/2005 | Katase | A24F 47/002 131/194 |
| 2006/0016453 A1 | 1/2006 | Kim | |
| 2006/0196518 A1* | 9/2006 | Hon | A24F 47/002 131/360 |
| 2007/0074734 A1 | 4/2007 | Braunshteyn et al. | |
| 2007/0102013 A1 | 5/2007 | Adams et al. | |
| 2007/0215167 A1 | 9/2007 | Crooks et al. | |
| 2008/0085103 A1 | 4/2008 | Beland et al. | |
| 2008/0092912 A1 | 4/2008 | Robinson et al. | |
| 2008/0257367 A1 | 10/2008 | Paterno et al. | |
| 2008/0276947 A1 | 11/2008 | Martzel | |
| 2008/0302374 A1 | 12/2008 | Wengert et al. | |
| 2009/0095311 A1 | 4/2009 | Hon | |
| 2009/0095312 A1 | 4/2009 | Herbrich et al. | |
| 2009/0126745 A1 | 5/2009 | Hon | |
| 2009/0188490 A1 | 7/2009 | Hon | |
| 2009/0230117 A1 | 9/2009 | Fernando et al. | |
| 2009/0272379 A1 | 11/2009 | Thorens et al. | |
| 2009/0283103 A1 | 11/2009 | Nielsen et al. | |
| 2009/0320863 A1 | 12/2009 | Fernando et al. | |
| 2010/0043809 A1 | 2/2010 | Magnon | |
| 2010/0083959 A1 | 4/2010 | Siller | |
| 2010/0200006 A1 | 8/2010 | Robinson et al. | |
| 2010/0229881 A1 | 9/2010 | Hearn | |
| 2010/0242974 A1 | 9/2010 | Pan | |
| 2010/0307518 A1 | 12/2010 | Wang | |
| 2010/0313901 A1 | 12/2010 | Fernando et al. | |
| 2011/0005535 A1 | 1/2011 | Xiu | |
| 2011/0011396 A1 | 1/2011 | Fang | |
| 2011/0036363 A1 | 2/2011 | Urtsev et al. | |
| 2011/0036365 A1 | 2/2011 | Chong et al. | |
| 2011/0094523 A1 | 4/2011 | Thorens et al. | |
| 2011/0126848 A1 | 6/2011 | Zuber et al. | |
| 2011/0155153 A1 | 6/2011 | Thorens et al. | |
| 2011/0155718 A1 | 6/2011 | Greim et al. | |
| 2011/0168194 A1 | 7/2011 | Hon | |
| 2011/0265806 A1 | 11/2011 | Alarcon et al. | |
| 2011/0309157 A1 | 12/2011 | Yang et al. | |
| 2012/0042885 A1 | 2/2012 | Stone et al. | |
| 2012/0060853 A1 | 3/2012 | Robinson et al. | |
| 2012/0111347 A1 | 5/2012 | Hon | |
| 2012/0132643 A1 | 5/2012 | Choi et al. | |
| 2012/0227752 A1 | 9/2012 | Alelov | |
| 2012/0231464 A1 | 9/2012 | Yu et al. | |
| 2012/0260927 A1 | 10/2012 | Liu | |
| 2012/0279512 A1 | 11/2012 | Hon | |
| 2012/0318882 A1 | 12/2012 | Abehasera | |
| 2013/0037041 A1 | 2/2013 | Worm et al. | |
| 2013/0056013 A1 | 3/2013 | Terry et al. | |
| 2013/0081625 A1 | 4/2013 | Rustad et al. | |
| 2013/0081642 A1* | 4/2013 | Safari | A24F 47/008 131/329 |
| 2013/0192619 A1 | 8/2013 | Tucker et al. | |
| 2013/0255702 A1 | 10/2013 | Griffith, Jr. et al. | |
| 2013/0306084 A1 | 11/2013 | Flick | |
| 2013/0319439 A1 | 12/2013 | Gorelick et al. | |
| 2013/0340750 A1 | 12/2013 | Thorens et al. | |
| 2013/0340775 A1* | 12/2013 | Juster | H04L 67/42 131/273 |
| 2014/0000638 A1 | 1/2014 | Sebastian et al. | |
| 2014/0060554 A1 | 3/2014 | Collett et al. | |
| 2014/0060555 A1 | 3/2014 | Chang et al. | |
| 2014/0096781 A1 | 4/2014 | Sears et al. | |
| 2014/0096782 A1 | 4/2014 | Ampolini et al. | |

(56) References Cited

U.S. PATENT DOCUMENTS

| | | |
|---|---|---|
| 2014/0109921 A1 | 4/2014 | Chen |
| 2014/0157583 A1 | 6/2014 | Ward et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2014/0345631 A1 | 11/2014 | Bowen et al. |
| 2015/0007838 A1 | 1/2015 | Fernando et al. |
| 2015/0053217 A1 | 2/2015 | Steingraber et al. |
| 2016/0037826 A1 | 2/2016 | Hearn et al. |
| 2016/0089508 A1 | 3/2016 | Smith et al. |

FOREIGN PATENT DOCUMENTS

| | | |
|---|---|---|
| CN | 1541577 | 11/2004 |
| CN | 2719043 | 8/2005 |
| CN | 200997909 | 1/2008 |
| CN | 101116542 | 2/2008 |
| CN | 101176805 | 5/2008 |
| CN | 201379072 | 1/2010 |
| DE | 10 2006 004 484 | 8/2007 |
| DE | 102006041042 | 3/2008 |
| DE | 20 2009 010 400 | 11/2009 |
| EP | 0 295 122 | 12/1988 |
| EP | 0 430 566 | 6/1991 |
| EP | 0 845 220 | 6/1998 |
| EP | 1 618 803 | 1/2006 |
| EP | 2 316 286 | 5/2011 |
| EP | 3 066 941 A1 | 9/2016 |
| GB | 2469850 | 11/2010 |
| WO | WO 1997/48293 | 12/1997 |
| WO | WO 2003/034847 | 5/2003 |
| WO | WO 2004/043175 | 5/2004 |
| WO | WO 2004/080216 | 9/2004 |
| WO | 2005/079894 A1 | 9/2005 |
| WO | WO 2005/099494 | 10/2005 |
| WO | WO 2007/078273 | 7/2007 |
| WO | WO 2007/131449 | 11/2007 |
| WO | WO 2009/105919 | 9/2009 |
| WO | WO 2009/155734 | 12/2009 |
| WO | WO 2010/003480 | 1/2010 |
| WO | WO 2010/045670 | 4/2010 |
| WO | WO 2010/073122 | 7/2010 |
| WO | WO 2010/118644 | 10/2010 |
| WO | WO 2010/140937 | 12/2010 |
| WO | WO 2011/010334 | 1/2011 |
| WO | 2012027350 A2 | 3/2012 |
| WO | WO 2012/072762 | 6/2012 |
| WO | WO 2012/100523 | 8/2012 |
| WO | WO 2013/089551 | 6/2013 |
| WO | 2013/152873 | 10/2013 |
| WO | 2015/079197 A1 | 6/2015 |

OTHER PUBLICATIONS

International Search Report dated Feb. 1, 2018 in International Application No. PCT/IB2017/054018 filed Jul. 3, 2017.
International Search Report dated Jan. 8, 2019 in International Application No. PCT/IB2017/054018 filed Jul. 3, 2017.

* cited by examiner

```
                          ┌─────────┐
                          │  START  │
                          └────┬────┘
                               ▼
   ┌───────────────────────────────────────────────────────┐
   │ ACTIVATING A FIRST ELEMENT AND SECOND ELEMENT CONTAINED WITHIN AT │
   │     LEAST ONE HOUSING OF AN AEROSOL DELIVERY DEVICE   │
   │                          402                          │
   └───────────────────────────┬───────────────────────────┘
                               ▼
   ┌───────────────────────────────────────────────────────┐
   │ AT THE FIRST ELEMENT AND SECOND ELEMENT SO ACTIVATED, VAPORIZING │
   │ COMPONENTS OF AN AEROSOL PRECURSOR COMPOSITION, AND THEREBY │
   │ FORMING RESPECTIVELY A CONDENSING VAPOR AND NON-CONDENSING VAPOR │
   │ COMBINABLE WITH AIR TO FORM AN AEROSOL IN RESPONSE TO A FLOW OF THE │
   │   AIR THROUGH AT LEAST A PORTION OF THE AT LEAST ONE HOUSING │
   │                          404                          │
   └───────────────────────────┬───────────────────────────┘
                               ▼
                          ┌─────────┐
                          │   END   │
                          └─────────┘
```

FIG. 4

```
                    ┌─────────┐
                    │  START  │
                    └────┬────┘
                         ▼
┌─────────────────────────────────────────────────────────────┐
│ ACTIVATING A FIRST ELEMENT AND SECOND ELEMENT CONTAINED     │
│         WITHIN AT LEAST ONE HOUSING OF AN AEROSOL           │
│                     DELIVERY DEVICE                         │
│                           502                               │
└─────────────────────────────┬───────────────────────────────┘
                              ▼
┌─────────────────────────────────────────────────────────────┐
│  AT THE SECOND ELEMENT SO ACTIVATED, VAPORIZING COMPONENTS  │
│  OF THE AEROSOL PRECURSOR COMPOSITION TO THEREBY FORM A     │
│                    NON-CONDENSING VAPOR                     │
│                           504                               │
└─────────────────────────────┬───────────────────────────────┘
                              ▼
┌─────────────────────────────────────────────────────────────┐
│   AT THE FIRST ELEMENT SO ACTIVATED, MODIFYING THE NON-     │
│  CONDENSING VAPOR, THE NON-CONDENSING VAPOR THEREFROM BEING │
│           COMBINABLE WITH THE AIR TO FORM AN AEROSOL        │
│                           506                               │
└─────────────────────────────┬───────────────────────────────┘
                              ▼
                         ┌─────────┐
                         │   END   │
                         └─────────┘
```

AEROSOL DELIVERY DEVICE WITH CONDENSING AND NON-CONDENSING VAPORIZATION

TECHNOLOGICAL FIELD

The present disclosure relates to aerosol delivery devices such as smoking articles that may utilize electrically generated heat for the production of aerosol (e.g., smoking articles commonly referred to as electronic cigarettes). The smoking articles may be configured to heat the aerosol precursor, which may incorporate materials that may be made or derived from tobacco or otherwise incorporate tobacco, the precursor being capable of forming an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar or pipe smoking, but without delivering considerable quantities of incomplete combustion and pyrolysis products that result from the burning of tobacco. To this end, there have been proposed numerous smoking products, flavor generators and medicinal inhalers that utilize electrical energy to vaporize or heat a volatile material, or attempt to provide the sensations of cigarette, cigar or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. No. 8,881,737 to Collett et al., which are incorporated herein by reference. See also, for example, the various types of smoking articles, aerosol delivery devices and electrically-powered heat generating sources referenced by brand name and commercial source in U.S. Pat. Pub. No. 2015/0216232 to Bless et al., which is incorporated herein by reference. Additionally, various types of electrically powered aerosol and vapor delivery devices also have been proposed in U.S. Pat. Pub. Nos. 2014/0096781 to Sears et al. and 2014/0283859 to Minskoff et al., as well as U.S. patent application Ser. No. 14/282,768 to Sears et al., filed May 20, 2014; Ser. No. 14/286,552 to Brinkley et al., filed May 23, 2014; Ser. No. 14/327,776 to Ampolini et al., filed Jul. 10, 2014; and Ser. No. 14/465,167 to Worm et al., filed Aug. 21, 2014; all of which are incorporated herein by reference.

It would be desirable to provide aerosol delivery devices with functionality for producing condensing and non-condensing vapor.

SUMMARY OF THE DISCLOSURE

The present disclosure relates to aerosol delivery devices, methods of forming such devices, and elements of such devices. The present disclosure thus includes, without limitation, the following example implementations. In some example implementations, an aerosol delivery device is provided that comprises at least one housing defining a reservoir for storing aerosol precursor composition. The aerosol delivery device also comprises a first element and second element contained within the at least one housing and configured to activate and vaporize components of the aerosol precursor composition to thereby form respectively a condensing vapor and non-condensing vapor. In response to a flow of air through at least a portion of the at least one housing, at least one of the condensing vapor or non-condensing vapor may be combinable with the air to form an aerosol.

In some example implementations of the aerosol delivery device of the preceding or any subsequent example implementation, or any combination thereof, the first element and second element are respectively a heater and electromechanical device configured to vaporize components of an aerosol precursor composition by respectively a heating action and mechanical action.

In some example implementations of the aerosol delivery device of any preceding or any subsequent example implementation, or any combination thereof, the first element and second element being contained within the at least one housing includes the first element and second element being removably coupled to the at least one housing.

In some example implementations of the aerosol delivery device of any preceding or any subsequent example implementation, or any combination thereof, further comprising a control valve configured to control a flow of aerosol precursor composition from the reservoir to the first element and second element.

In some example implementations of the aerosol delivery device of any preceding or any subsequent example implementation, or any combination thereof, the reservoir is refillable, and the at least one housing further defines a port mateable with only a corresponding container of aerosol precursor composition for refilling the reservoir.

In some example implementations of the aerosol delivery device of any preceding or any subsequent example implementation, or any combination thereof, the first element includes a liquid transport element configured to transport aerosol precursor composition from the reservoir, and a heater configured to activate and vaporize components of the aerosol precursor composition so transported by the liquid transport element.

In some example implementations of the aerosol delivery device of any preceding or any subsequent example implementation, or any combination thereof, the second element being configured to form and direct the non-condensing vapor to the first element, and the first element being configured to activate and vaporize components of the non-condensing vapor to thereby form the condensing vapor.

In some example implementations of the aerosol delivery device of any preceding or any subsequent example implementation, or any combination thereof, a distance between the first element and second element is between one (1) millimeter and three (3) centimeters inclusive.

In some example implementations of the aerosol delivery device of any preceding or any subsequent example implementation, or any combination thereof, the first element being configured to activate includes being configured to activate simultaneously with the non-condensing vapor being directed to the first element.

In some example implementations of the aerosol delivery device of any preceding or any subsequent example implementation, or any combination thereof, the flow of air through at least the portion of the at least one housing is transversely or longitudinally directed toward the non-condensing vapor based on a velocity thereof.

In some example implementations, an aerosol delivery device is provided that comprises at least one housing defining a reservoir for storing aerosol precursor composition. The aerosol delivery device also comprises a first element and second element contained within the at least one housing. In response to a flow of air through at least a portion of the at least one housing, the second element is configured to activate and vaporize components of the aerosol precursor composition to thereby form a non-condensing vapor, and the first element is configured to modify the non-condensing vapor. The non-condensing vapor therefrom is combinable with the air to form an aerosol.

In some example implementations of the aerosol delivery device of the preceding or any subsequent example implementation, or any combination thereof, the first element and second element are respectively a vapor modification element and electromechanical device. The electromechanical device is configured to vaporize components of an aerosol precursor composition by a mechanical action, and the vapor modification element is configured to modify the non-condensing vapor by a moisture removal action.

In some example implementations of the aerosol delivery device of any preceding or any subsequent example implementation, or any combination thereof, the first element and second element are respectively a vapor modification element and electromechanical device. The electromechanical device is configured to vaporize components of an aerosol precursor composition by a mechanical action, and the vapor modification element is configured to modify the non-condensing vapor by injecting a volatile flavor into the non-condensing vapor.

In some example implementations of the aerosol delivery device of any preceding or any subsequent example implementation, or any combination thereof, the first element is a vapor modification element including at least one of a drying tube or flavor modifier respectively configured to modify the non-condensing vapor by a moisture removal action or flavor injection action.

In some example implementations of the aerosol delivery device of any preceding or any subsequent example implementation, or any combination thereof, further comprises a third element. In response to a flow of air through at least a portion of the at least one housing, the third element is configured to activate and vaporize components of the aerosol precursor composition to thereby form a condensing vapor, and the first element is further configured to modify the condensing vapor or non-condensing vapor. At least one of the condensing vapor or non-condensing vapor therefrom is combinable with the air to form an aerosol.

In some example implementations of the aerosol delivery device of any preceding or any subsequent example implementation, or any combination thereof, the second and third elements are respectively a electromechanical device and heater configured to vaporize components of an aerosol precursor composition by respectively a mechanical action and heating action, and the first element is a vapor modification element configured to modify the condensing or non-condensing vapor by injecting a volatile flavor into the condensing or non-condensing vapor.

In some example implementations, a method is provided for controlling an aerosol delivery device comprising at least one housing defining a reservoir for storing aerosol precursor composition, and a first and second element contained within the at least one housing. The method includes activating the first element and second element. At the first element and second element so activated, the method also includes vaporizing components of the aerosol precursor composition, and thereby forming respectively a condensing vapor and non-condensing vapor, the first element and second element activating and vaporizing components of the aerosol precursor composition in response to a flow of air through at least a portion of the at least one housing. At least one of the condensing vapor or non-condensing vapor is combinable with the air to form an aerosol.

In some example implementations of the method of the preceding or any subsequent example implementation, or any combination thereof, the first element and second element are respectively a heater and electromechanical device, and vaporizing components of the aerosol precursor composition includes vaporizing components of the aerosol precursor composition by respectively a heating action and mechanical action.

In some example implementations, a method is provided for controlling an aerosol delivery device comprising at least one housing defining a reservoir for storing aerosol precursor composition, and a first and second element contained within the at least one housing. The method includes activating the first element and second element. At the second element so activated, the method also includes vaporizing components of the aerosol precursor composition to thereby form a non-condensing vapor in response to a flow of air through at least a portion of the at least one housing. At the first element so activated, the method also includes modifying the non-condensing vapor. The non-condensing vapor therefrom is combinable with the air to form an aerosol.

In some example implementations of the method of the preceding or any subsequent example implementation, or any combination thereof, the first element is a vapor modification element including at least one of a drying tube or flavor modifier respectively configured to modify the non-condensing vapor by a moisture removal action or flavor injection action, and the second element is a electromechanical device configured to vaporize components of an aerosol precursor composition by a mechanical action.

These and other features, aspects, and advantages of the present disclosure will be apparent from a reading of the following detailed description together with the accompanying drawings, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as intended, namely to be combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying drawings which illustrate, by way of example, the principles of some described example implementations.

BRIEF DESCRIPTION OF THE FIGURES

Figure 1:
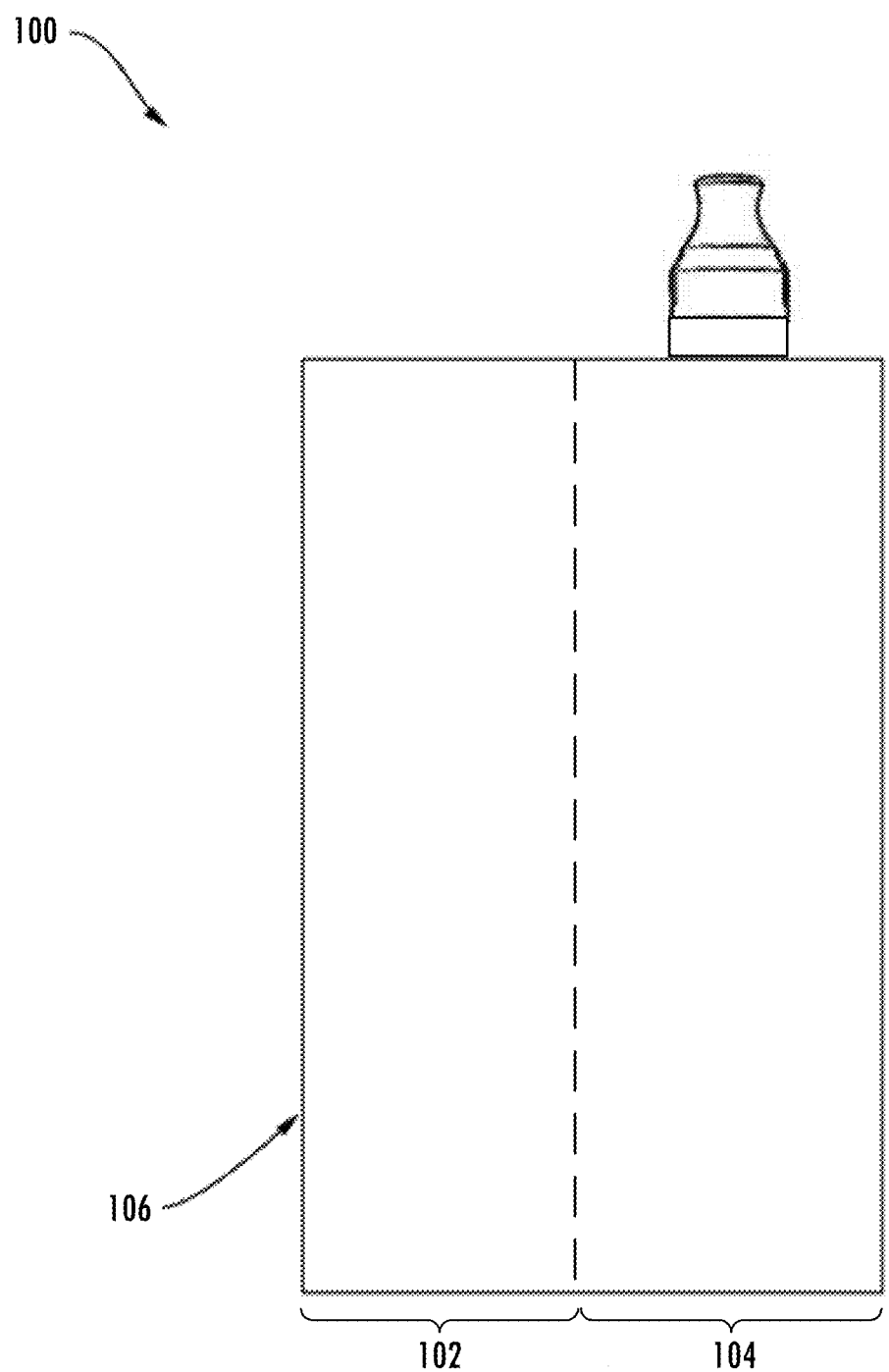
Figure 2:
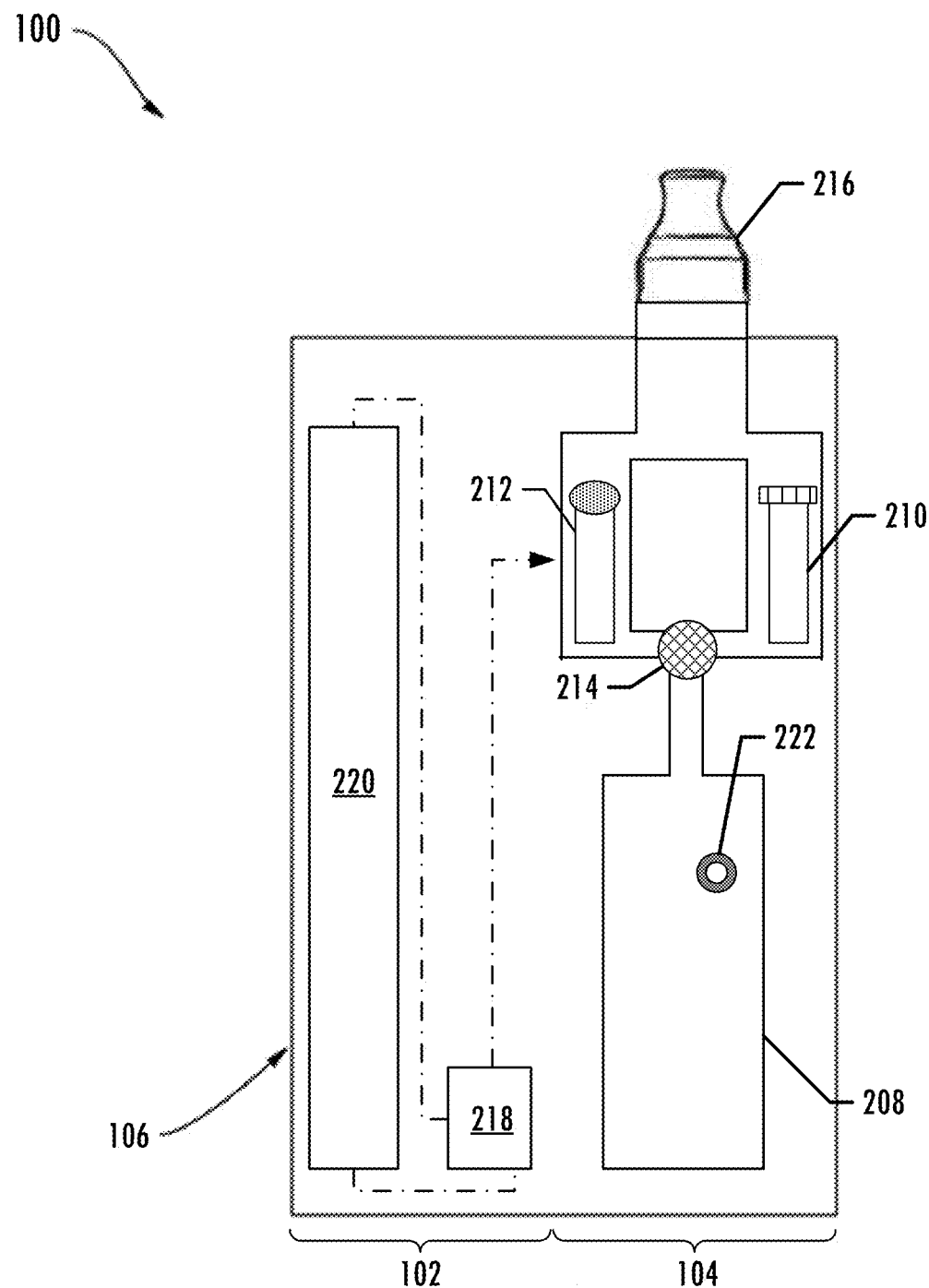
Figure 3A:
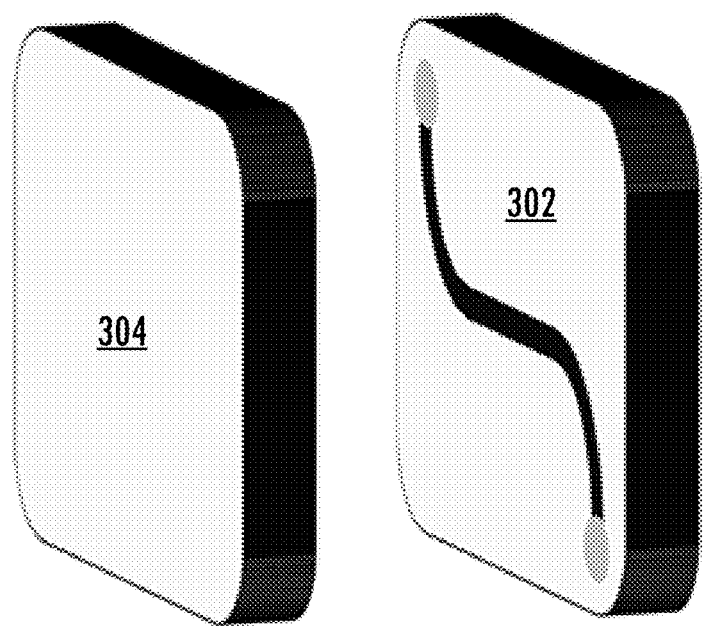
Figure 3B:
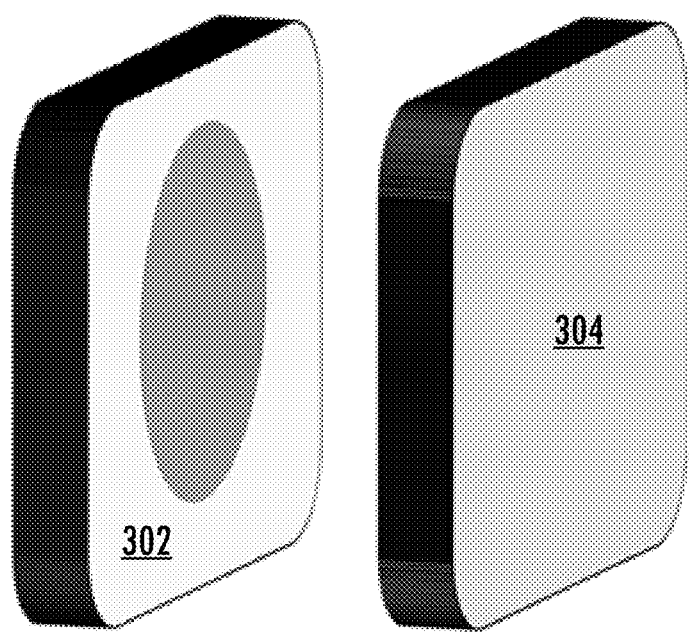

Having thus described the disclosure in the foregoing general terms, reference will now be made to the accompanying drawings, which are not necessarily drawn to scale, and wherein:

FIG. 1 illustrates a front view of an aerosol delivery device with condensing and non-condensing vaporization functionality, according to an example implementation of the present disclosure;

FIG. 2 illustrates a sectional view of the aerosol delivery device of FIG. 1;

FIGS. 3A and 3B illustrate a first and second element of the aerosol delivery device of FIG. 2, according to an example implementation of the present disclosure;

FIG. 4 illustrates various operations in a method for controlling an aerosol delivery device, according to an example implementation of the present disclosure; and FIG. 5 illustrates various operations in a method for controlling an aerosol delivery device, according to an example implementation of the present disclosure.

DETAILED DESCRIPTION

The present disclosure will now be described more fully hereinafter with reference to example implementations thereof. These example implementations are described so that this disclosure will be thorough and complete, and will fully convey the scope of the disclosure to those skilled in the art. Indeed, the disclosure may be embodied in many different forms and should not be construed as limited to the implementations set forth herein; rather, these implementations are provided so that this disclosure will satisfy applicable legal requirements. As used in the specification and the appended claims, the singular forms "a," "an," "the" and the like include plural referents unless the context clearly dictates otherwise. Also, for example, reference may be made herein to quantitative measures, values, relationships or the like. Unless otherwise stated, any one or more if not all of these may be absolute or approximate to account for acceptable variations that may occur, such as those due to engineering tolerances or the like.

As described hereinafter, example implementations of the present disclosure relate to aerosol delivery systems. Aerosol delivery systems according to the present disclosure use electrical energy to power elements that vaporize a material (preferably without combusting the material to any significant degree and/or without significant chemical alteration of the material) to form an inhalable substance; and components of such systems have the form of articles that most preferably are sufficiently compact to be considered handheld devices. That is, use of components of preferred aerosol delivery systems does not result in the production of smoke in the sense that aerosol results principally from by-products of combustion or pyrolysis of tobacco, but rather, use of those preferred systems results in the production of vapors resulting from volatilization or vaporization of certain components incorporated therein. In some example implementations, components of aerosol delivery systems may be characterized as electronic cigarettes, and those electronic cigarettes most preferably incorporate tobacco and/or components derived from tobacco, and hence deliver tobacco derived components in aerosol form.

Aerosol generating pieces of certain preferred aerosol delivery systems may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol generating piece of the present disclosure can hold and use that piece much like a smoker employs a traditional type of smoking article, draw on one end of that piece for inhalation of aerosol produced by that piece, take or draw puffs at selected intervals of time, and the like.

Aerosol delivery systems of the present disclosure also can be characterized as being vapor-producing articles or medicament delivery articles. Thus, such articles or devices can be adapted so as to provide one or more substances (e.g., flavors and/or pharmaceutical active ingredients) in an inhalable form or state. For example, inhalable substances can be substantially in the form of a vapor (i.e., a substance that is in the gas phase at a temperature lower than its critical point). Alternatively, inhalable substances can be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like.

Aerosol delivery systems of the present disclosure generally include a number of components provided within an outer body or shell, which may be referred to as a housing. The overall design of the outer body or shell can vary, and the format or configuration of the outer body that can define the overall size and shape of the aerosol delivery device can vary. Aerosol delivery devices are often configured in a manner that mimics aspects of certain traditional smoking devices such as cigarettes or cigars. In this regard, aerosol delivery devices typically define a substantially cylindrical configuration. Typically, an elongated body resembling the shape of a cigarette or cigar can be a formed from a single, unitary housing or the elongated housing can be formed of two or more separable bodies. For example, an aerosol delivery device can comprise an elongated shell or body that can be substantially tubular in shape and, as such, resemble the shape of a conventional cigarette or cigar. Aerosol delivery devices often include a control portion and a cartridge which attach in an end-to-end relationship to define the substantially cylindrical configuration. In an alternative implementation, the housing may define an ergonomic shape configured to comfortably fit within a user's hand. The shape of the housing, however, is not limited and may be any shape that accommodates the various elements as described herein. In some implementations, the housing may be expressly non-cylindrical.

While such configurations may provide a look and feel that is similar to traditional smoking articles, these configurations may suffer from certain detriments. For example, cylindrically-configured aerosol delivery devices may not define attachment points usable to retain the aerosol delivery device in a desired position when not in use. Further, the cylindrical configuration may result in the mouthpiece being exposed to the surrounding environment and therefore susceptible to contamination. Accordingly, it may be desirable to provide aerosol delivery devices in configurations that differ from shapes associated with traditional smoking articles.

In one example, all of the components of the aerosol delivery device are contained within one housing. Alternatively, an aerosol delivery device can comprise two or more housings that are joined and are separable. For example, an aerosol delivery device can possess at one end a control portion comprising a housing containing one or more reusable components (e.g., an accumulator such as a rechargeable battery and/or capacitor, and various electronics for controlling the operation of that article), and at the other end and removably coupleable thereto, an outer body or shell containing a disposable portion (e.g., a disposable flavor-containing cartridge).

Aerosol delivery systems of the present disclosure most preferably comprise some combination of a power source (i.e., an electrical power source), at least one control component (e.g., means for actuating, controlling, regulating and ceasing power for vaporization, such as by controlling electrical current flow from the power source to other components of the article—e.g., a microprocessor, individually or as part of a microcontroller), an aerosol precursor composition (e.g., commonly a liquid capable of yielding an aerosol upon application of sufficient heat or mechanical action, such as ingredients commonly referred to as "smoke juice," "e-liquid" and "e-juice"), one or more elements for vaporization of components of the aerosol precursor composition (e.g., a heater, electromechanical device or the like, which alone or in combination with one or more further elements may be commonly referred to as an "atomizer"), and a mouth end region or tip for allowing draw upon the aerosol delivery device for aerosol inhalation (e.g., a defined airflow path through the article such that aerosol generated can be withdrawn therefrom upon draw).

In various examples, an aerosol delivery device can comprise a reservoir configured to retain the aerosol precursor composition. The reservoir particularly can be formed of a porous material (e.g., a rigid porous material or primarily fibrous material) and thus may be referred to as a porous substrate.

A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material, regenerated cellulose, organic cotton, or polyethylene terephthalate can be used. In other example implementations, a carbon material can be used. In further example implementations, organic cotton, polyethylene terephthalate, regenerated cellulose, porous ceramic, or porous sintered ceramic can be used. A reservoir may be substantially in the form of a container and may include a fibrous material included therein. In other implementations, the reservoir may be formed of a glass, plastic, or other materials not explicitly set forth herein.

In some implementations, the aerosol delivery device can include an indicator, which may comprise one or more light emitting diodes or a graphical user interface via a display. The indicator can be in communication with the control component through a connector circuit and illuminate, for example, during a user draw on the mouth end as detected by the flow sensor.

More specific formats, configurations and arrangements of components within the aerosol delivery systems of the present disclosure will be evident in light of the further disclosure provided hereinafter. Additionally, the selection and arrangement of various aerosol delivery system components can be appreciated upon consideration of the commercially available electronic aerosol delivery devices, such as those representative products referenced in background art section of the present disclosure.

FIG. 1 illustrates a front view of an aerosol delivery device 100, and FIG. 2 illustrates a modified sectional view through the aerosol delivery device, according to an example implementation of the present disclosure. As illustrated, the aerosol delivery device may include a control portion 102 and a tank portion 104. In particular, FIG. 1 illustrates the control portion and the tank portion coupled to one another. The control portion and the tank portion may be permanently or detachably aligned in a functioning relationship. Various mechanisms may connect the tank portion to the control portion to result in a threaded engagement, a press-fit engagement, an interference fit, a magnetic engagement or the like. In some examples, as shown, the aerosol delivery device may be generally rectangular. In other examples, the aerosol delivery device may be substantially rod-like, substantially tubular shaped, or substantially cylindrically shaped when the tank portion and the control portion are in an assembled configuration. In yet other examples, further shapes and dimensions are encompassed—e.g., a triangular cross-section, multifaceted shapes, or the like.

The control portion 102 and tank portion 104 may include and/or be defined within a unitary housing 106 or outer body or separate, respective housings or outer bodies, which may be formed of any of a number of different materials. The housing may be formed of any combination of suitable, structurally-sound materials. In some examples, the housing may be formed of at least one of a metal or alloy, such as stainless steel, aluminum or the like. Other suitable materials include various plastics (e.g., polycarbonate or a copolyester), substantially biodegradable plastics (e.g., polyhydroxyalkonates), metal-plating over plastic, glass, and the like.

In some example implementations, one or both of the control portion 102 or the tank portion 104 of the aerosol delivery device 100 may be referred to as being disposable or as being reusable. The aerosol delivery device may include various other components disposed within the control portion or tank portion or otherwise coupled thereto. These components may be distributed between the control portion and the tank portion in any of various manners. For example, the control portion may have a replaceable battery or removable battery or a rechargeable battery and thus may be combined with any type of recharging technology, including connection to a typical wall charger, connection to a car charger (i.e., a cigarette lighter receptacle), connection to a computer, such as through a universal serial bus (USB) cable or connector, or connection to a photovoltaic cell (sometimes referred to as a solar cell) or solar panel of solar cells. For example, an adaptor including a USB connector at one end and a control portion connector at an opposing end is disclosed in U.S. Pat. Pub. No. 2014/0261495 to Novak et al., which is incorporated herein by reference in its entirety.

In one example implementation, the control portion 102 and tank portion 104 forming the aerosol delivery device 100 may be permanently and/or removably coupled to one another. Examples of aerosol delivery devices that may be configured to be disposable and/or which may include first and second outer bodies that are configured for permanent coupling are disclosed in U.S. Pat. App. No. 2015/0216232 to Bless et al., which is incorporated herein by reference in its entirety. In another example implementation, the tank portion and control portion may be configured in a single-piece, non-detachable form and may incorporate the components, aspects, and features disclosed herein. However, in another example implementation, the control portion and tank portion may be configured to be separable such that, for example, the tank portion may be refilled or replaced.

FIG. 2 illustrates a more particular example of the aerosol delivery device 100 in which the components are representative of the components that may be present in a suitable control portion 102 and a tank portion 104 and are not intended to limit the scope of control portion and tank portion components that are encompassed by the present disclosure.

The tank portion 104 may include a reservoir 208 configured to retain the aerosol precursor composition, and include one or more elements such as elements 210, 212 for vaporization of components of aerosol precursor composition, which elements may at times be referred to as vaporization elements. As explained in greater detail below, these vaporization elements may include first and second elements, and in some examples, these elements may be respectively a heater and electromechanical device configured to vaporize components of an aerosol precursor composition by respectively a heating action and mechanical action. In various configurations, the tank portion structure may be referred to as a cartridge; and accordingly, the terms "tank portion," "tank", "cartridge" and the like may be used interchangeably to refer to a shell or other housing enclosing a reservoir for aerosol precursor composition, and including a vaporization element.

In some example, the reservoir 208 of the tank portion 104 may comprise a refillable reservoir. The reservoir may be configured to retain the aerosol precursor composition. In some example implementations, the reservoir particularly can be formed of a porous material (e.g., a fibrous material) and thus may be referred to as a porous substrate (e.g., a fibrous substrate). A fibrous substrate useful as a reservoir in an aerosol delivery device can be a woven or nonwoven material formed of a plurality of fibers or filaments and can be formed of one or both of natural fibers and synthetic fibers. For example, a fibrous substrate may comprise a fiberglass material. In particular examples, a cellulose acetate material can be used. In other example implementations, a carbon material can be used. A reservoir may be substantially in the form of a container and may include a fibrous material included therein. In other implementations, the reservoir may be formed of a glass, ceramic, plastic, or other materials not explicitly set forth herein.

The reservoir 208 may be in fluid communication with a liquid transport element adapted to wick or otherwise transport an aerosol precursor composition stored in the reservoir housing to the vaporization elements 210, 212. In some examples, a valve 214 may be positioned between the reservoir and the vaporization elements, and configured to control an amount of aerosol precursor composition passed or delivered from the reservoir to the vaporization elements.

A mouthpiece 216 having an opening defined therein may be coupled to the housing 106 (e.g., at the mouth end) to allow for egress of formed aerosol from the tank portion.

The tank portion 104 may also include one or more electronic components, which may include an integrated circuit, a memory component, a sensor, or the like. The electronic components may be adapted to communicate with a control component 218 of the control portion 102 and/or with an external device by wired or wireless means. The electronic components may be positioned anywhere within the tank portion.

In addition to the control component 218, the control portion 102 may include a power source 220, and one or more indicators such as light-emitting diodes (LEDs), and such components can be variably aligned. The power source may include, for example, a battery (single-use or rechargeable), supercapacitor or the like. Further indicators (e.g., a haptic feedback component, an audio feedback component, or the like) can be included in addition to or as an alternative to the LED. Additional representative types of components that yield visual cues or indicators, such as light emitting diode (LED) components, and the configurations and uses thereof, are described in U.S. Pat. No. 5,154,192 to Sprinkel et al.; U.S. Pat. No. 8,499,766 to Newton and U.S. Pat. No. 8,539,959 to Scatterday; and U.S. patent application Ser. No. 14/173,266, filed Feb. 5, 2014, to Sears et al.; which are incorporated herein by reference.

The control component 218 may be configured to direct electrical power from the power source 220 to the vaporization elements 210, 212 to vaporize component of the aerosol precursor composition retained in the tank portion 104 and produce a vapor, which may occur during a user draw on a mouthpiece 216 of the housing. The control component may include a number of electronic components, and in some examples may be formed of an electronic or printed circuit board (PCB) that supports and electrically connects the electronic components. Examples of suitable electronic components include a microprocessor or processor core, memory device, application-specific integrated circuit (ASIC), field-programmable gate array (FPGA) or the like and the like.

In some examples, the control component 218 may include a microcontroller with an integrated processor core and memory, and which may further include one or more integrated input/output peripherals. In some examples, the control component may be coupled to a communication interface to enable wireless communication with one or more networks, computing devices or other appropriately-enabled devices. Examples of suitable communication interfaces are disclosed in U.S. patent application Ser. No. 14/638,562, filed Mar. 4, 2015, to Marion et al., the content of which is incorporated by reference in its entirety. And examples of suitable manners according to which the aerosol delivery device may be configured to wirelessly communicate are disclosed in U.S. patent application Ser. No. 14/327,776, filed Jul. 10, 2014, to Ampolini et al., and U.S. patent application Ser. No. 14/609,032, filed Jan. 29, 2015, to Henry, Jr. et al., each of which is incorporated herein by reference in its entirety.

The control portion 102 and the tank portion 104 may include components adapted to facilitate a fluid engagement therebetween. The control portion can include a connector. The tank portion can be adapted to engage the connector and can include a projection adapted to fit within the connector. Such engagement can facilitate a stable connection between the control portion and the tank portion as well as establish an electrical connection between the power source 220 and control component 218 in the control portion, and the vaporization elements 210, 212, in the tank portion. Further, the control portion can include an air intake, which may be a notch in a shell of the control portion where it connects to the connector that allows for passage of ambient air around the connector and into the shell where it then passes through the connector and into the tank portion through the projection.

A connector and a base useful according to the present disclosure are described in U.S. Pat. App. Pub. No. 2014/0261495 to Novak et al., which is incorporated herein by reference in its entirety. However, various other examples of structures, shapes and components may be employed to couple the base to the connector. In some examples the connection between the base of the tank portion 104 and the connector of the control portion 102 may be substantially permanent, whereas in other examples the connection therebetween may be releasable such that, for example, the control portion may be reused with one or more additional tank portions that may be disposable and/or refillable.

The reservoir 208 illustrated in FIG. 2 can be a container or can be a reservoir, as presently described. For example, the reservoir can be substantially formed into the shape of a tube encircling the interior of the tank portion, in this example. An aerosol precursor composition can be retained in the reservoir. Liquid components, for example, can be retained by the reservoir. The reservoir can be in fluid connection with the liquid transport element. The liquid transport element can transport the aerosol precursor composition stored in the reservoir via capillary action to the vaporization elements 210, 212 that is in the form of a metal wire coil in some examples. As such, the vaporization elements are in arrangement with the liquid transport element. Example implementations of reservoirs and transport elements useful in aerosol delivery devices according to the present disclosure are further described below, and such reservoirs and/or transport elements can be incorporated into devices as described herein. In particular, specific combinations of vaporization elements and transport elements as further described below may be incorporated into devices.

In use, when a user draws on the aerosol delivery device 100, airflow is detected by a flow sensor, and the vaporization elements 210, 212 are activated to vaporize components of the aerosol precursor composition. In some implementations, a manual button may be used exclusively, or in combination with a flow sensor, to activate the vaporization elements. Alternatively, the manual button may be depressed to activate the vaporization elements in lieu of a flow sensor. Drawing upon the mouthpiece 216 of the aerosol delivery device causes ambient air to enter the air intake and pass through a connector and a central opening in the tank portion 104. In the tank portion, the drawn air combines with the formed vapor to form an aerosol. The aerosol is whisked, aspirated or otherwise drawn away from the vaporization elements and out the opening in the mouthpiece of the aerosol delivery device.

Although not separately shown, the aerosol delivery device 100 may further include input element to allow a user to control functions of the device and/or for output of information to a user. For example, a user may utilize the input element to vaporize an aerosol precursor composition and/or activate an on/off function. The input element may comprise a pushbutton or other switch configured to receive an input from a user. When the input element is actuated, the aerosol delivery device may produce an output corresponding to a status of the aerosol delivery device. For example, the aerosol delivery device may output sound, vibration, or light. Any component or combination of components may be utilized as an input for controlling the function of the device. For example, one or more pushbuttons may be used as described in U.S. patent application Ser. No. 14/193,961, filed Feb. 28, 2014, to Worm et al., which is incorporated herein by reference. Likewise, a touchscreen may be used as described in U.S. patent application Ser. No. 14/643,626, filed Mar. 10, 2015, to Sears et al., which is incorporated herein by reference. As a further example, components adapted for gesture recognition based on specified movements of the aerosol delivery device may be used as an input. See U.S. patent application Ser. No. 14/565,137, filed Dec. 9, 2014, to Henry et al., which is incorporated herein by reference.

In some example implementations, a computing device such as a mobile computer (e.g., smartphone, tablet computer) may be used as an input element in addition to or in lieu of an input element on the aerosol delivery device itself. In particular, the aerosol delivery device 100 may be wired to the computer or other device, such as via use of a USB cord or similar protocol. The aerosol delivery device also may communicate with a computer or other device acting as an input via wireless communication. See, for example, the systems and methods for controlling a device via a read request as described in U.S. patent application Ser. No. 14/327,776, filed Jul. 10, 2014, to Ampolini et al., the disclosure of which is incorporated herein by reference. In such implementations, application software may be used in connection with the computing device to input control instructions to the aerosol delivery device, such control instructions including, for example, the ability to form an aerosol of specific composition by choosing the nicotine content and/or content of further flavors to be included.

In some examples, the aerosol delivery device 100 may include a number of additional hardware-implemented or software-controlled functions. For example, the aerosol delivery device may include a battery protection circuit configured to detect battery input, loads on the battery terminals, and charging input. The battery protection circuit may include short-circuit protection and under-voltage lock out. The aerosol delivery device may also include components for ambient temperature measurement, and its control component 218 may be configured to control at least one functional element to inhibit battery charging if the ambient temperature is below a certain temperature (e.g., 0° C.) or above a certain temperature (e.g., 45° C.) prior to start of charging or during charging.

Power delivery from the power source 220 may vary over the course of each puff on the device 100 according to a power control mechanism. The device may include a "long puff" safety timer such that in the event that a user or an inadvertent mechanism causes the device to attempt to puff continuously, the control component 218 may control at least one functional element to terminate the puff automatically after some period of time (e.g., four seconds). Further, the time between puffs on the device may be restricted to greater than a period of time (e.g., one hundred (100) milliseconds). A watchdog safety timer may automatically reset the aerosol delivery device if its control component or software running on it becomes unstable and does not service the timer within an appropriate time interval (e.g., eight seconds). Further safety protection may be provided in the event of a defective or otherwise failed flow sensor, such as by permanently disabling the aerosol delivery device in order to prevent inadvertent vaporization. A puffing limit switch may deactivate the device in the event of a pressure sensor fail causing the device to continuously activate without stopping after the four second maximum puff time.

The various components of an aerosol delivery device according to the present disclosure can be chosen from components described in the art and commercially available. Examples of batteries that can be used according to the disclosure are described in U.S. Pat. Pub. No. 2010/0028766 to Peckerar et al., the disclosure of which is incorporated herein by reference in its entirety.

The aerosol delivery device 100 most preferably incorporates the control component 218 or another control mechanism for controlling the amount of electric power to the vaporization elements 210, 212 during draw. In some implementations, the control component may effect control of different power settings on the aerosol delivery device. For example, at least a low, medium, and high power setting may be controlled for adjusting aerosol production within the aerosol delivery device. Representative types of electronic components, structure and configuration thereof, features thereof, and general methods of operation thereof, are described in U.S. Pat. No. 4,735,217 to Gerth et al., U.S. Pat.

No. 4,947,874 to Brooks et al., U.S. Pat. No. 5,372,148 to McCafferty et al., U.S. Pat. No. 6,040,560 to Fleischhauer et al., U.S. Pat. No. 7,040,314 to Nguyen et al., U.S. Pat. No. 8,205,622 to Pan, U.S. Pat. App. Pub. No. 2009/0230117 to Fernando et al., U.S. Pat. App. Pub. No. 2014/0060554 to Collet et al., U.S. Pat. App. Pub. No. 2014/0270727 to Ampolini et al., and U.S. patent application Ser. No. 14/209,191 to Henry et al., filed Mar. 13, 2014, all of which are incorporated herein by reference in their entireties.

The aerosol delivery device 100 can also incorporate a flow sensor or another sensor or detector for control of supply of electric power to the vaporization elements 210, 212 when aerosol generation is desired (e.g., upon draw during use). As such, for example, there is provided a manner or method of turning off the power supply to the vaporization elements when the aerosol delivery device is not be drawn upon during use, and for turning on the power supply to actuate or trigger the vaporization of aerosol precursor composition by the vaporization elements during draw. Additional representative types of sensing or detection mechanisms, structure and configuration thereof, components thereof, and general methods of operation thereof, are described in U.S. Pat. No. 5,261,424 to Sprinkel, Jr., U.S. Pat. No. 5,372,148 to McCafferty et al., and PCT Pat. App. Pub. No. WO 2010/003480 to Flick, all of which are incorporated herein by reference in their entireties.

Representative types of substrates, reservoirs or other components for supporting the aerosol precursor are described in U.S. Pat. No. 8,528,569 to Newton, U.S. Pat. App. Pub. No. 2014/0261487 to Chapman et al., U.S. patent application Ser. No. 14/011,992 to Davis et al., filed Aug. 28, 2013, and U.S. patent application Ser. No. 14/170,838 to Bless et al., filed Feb. 3, 2014, all of which are incorporated herein by reference in their entireties. Additionally, various wicking materials, and the configuration and operation of those wicking materials within certain types of electronic cigarettes, are set forth in U.S. Pat. App. Pub. No. 2014/0209105 to Sears et al., which is incorporated herein by reference in its entirety.

For aerosol delivery systems that are characterized as electronic cigarettes, the aerosol precursor composition most preferably incorporates tobacco or components derived from tobacco. In one regard, the tobacco may be provided as parts or pieces of tobacco, such as finely ground, milled or powdered tobacco lamina. In another regard, the tobacco may be provided in the form of an extract, such as a spray dried extract that incorporates many of the water soluble components of tobacco. Alternatively, tobacco extracts may have the form of relatively high nicotine content extracts, which extracts also incorporate minor amounts of other extracted components derived from tobacco. In another regard, components derived from tobacco may be provided in a relatively pure form, such as certain flavoring agents that are derived from tobacco. In one regard, a component that is derived from tobacco, and that may be employed in a highly purified or essentially pure form, is nicotine (e.g., pharmaceutical grade nicotine).

The aerosol precursor composition, also referred to as a vapor precursor composition, may comprise a variety of components including, by way of example, a polyhydric alcohol (e.g., glycerin, propylene glycol, or a mixture thereof), nicotine, tobacco, tobacco extract, and/or flavorants. Various components that may be included in the aerosol precursor composition are described in U.S. Pat. No. 7,726,320 to Robinson et al., which is incorporated herein by reference in its entirety. Additional representative types of aerosol precursor compositions are set forth in U.S. Pat. No. 4,793,365 to Sensabaugh, Jr. et al., U.S. Pat. No. 5,101,839 to Jakob et al., U.S. Pat. No. 6,779,531 to Biggs et al., U.S. Pat. App. Pub. No. 2013/0008457 to Zheng et al., and *Chemical and Biological Studies on New Cigarette Prototypes that Heat Instead of Burn Tobacco*, R. J. Reynolds Tobacco Company Monograph (1988), all of which are incorporated herein by reference in their entireties.

Representative types of aerosol precursor components and formulations also are set forth and characterized in U.S. Pat. No. 7,217,320 to Robinson et al.; 2013/0213417 to Chong et al.; 2014/0060554 to Collett et al.; 2015/0020823 to Lipowicz et al.; and 2015/0020830 to Koller, as well as WO 2014/182736 to Bowen et al, the disclosures of which are incorporated herein by reference. Other aerosol precursors that may be employed include the aerosol precursors that have been incorporated in the VUSE® product by R. J. Reynolds Vapor Company, the BLU™ product by Imperial Tobacco Group PLC, the MISTIC MENTHOL product by Mistic Ecigs, and the VYPE product by CN Creative Ltd. Also desirable are the so-called "smoke juices" for electronic cigarettes that have been available from Johnson Creek Enterprises LLC.

The amount of aerosol precursor that is incorporated within the aerosol delivery system is such that the aerosol generating piece provides acceptable sensory and desirable performance characteristics. For example, it is highly preferred that sufficient amounts of aerosol forming material (e.g., glycerin and/or propylene glycol), be employed in order to provide for the generation of a visible mainstream aerosol that in many regards resembles the appearance of tobacco smoke. The amount of aerosol precursor within the aerosol generating system may be dependent upon factors such as the number of puffs desired per aerosol generating piece. Typically, the amount of aerosol precursor incorporated within the aerosol delivery system, and particularly within the aerosol generating piece, is less than about 5 grams, generally less than about 2.5 grams, often less than about 2 grams and frequently less than about 1 grams.

Additional representative types of components that yield visual cues or indicators may be employed in the aerosol delivery device 100, such as LEDs and related components, auditory elements (e.g., speakers), vibratory elements (e.g., vibration motors) and the like. Examples of suitable LED components, and the configurations and uses thereof, are described in U.S. Pat. No. 5,154,192 to Sprinkel et al., U.S. Pat. No. 8,499,766 to Newton, U.S. Pat. No. 8,539,959 to Scatterday, and U.S. patent application Ser. No. 14/173,266 to Sears et al., filed Feb. 5, 2014, all of which are incorporated herein by reference in their entireties.

Yet other features, controls or components that can be incorporated into aerosol delivery devices of the present disclosure are described in U.S. Pat. No. 5,967,148 to Harris et al., U.S. Pat. No. 5,934,289 to Watkins et al., U.S. Pat. No. 5,954,979 to Counts et al., U.S. Pat. No. 6,040,560 to Fleischhauer et al., U.S. Pat. No. 8,365,742 to Hon, U.S. Pat. No. 8,402,976 to Fernando et al., U.S. Pat. App. Pub. No. 2005/0016550 to Katase, U.S. Pat. App. Pub. No. 2010/0163063 to Fernando et al., U.S. Pat. App. Pub. No. 2013/0192623 to Tucker et al., U.S. Pat. App. Pub. No. 2013/0298905 to Leven et al., U.S. Pat. App. Pub. No. 2013/0180553 to Kim et al., U.S. Pat. App. Pub. No. 2014/0000638 to Sebastian et al., U.S. Pat. App. Pub. No. 2014/0261495 to Novak et al., and U.S. Pat. App. Pub. No. 2014/0261408 to DePiano et al., all of which are incorporated herein by reference in their entireties.

As previously indicated, the control component 218 of the aerosol delivery device 100 may be configured to direct electrical power from the power source 220 to the vaporization elements 210, 212 to vaporize aerosol precursor composition retained in the tank portion 104 and thereby form a vapor, which may occur during a user draw on a mouthpiece 216 of the tank portion. In the tank portion, the drawn air may be combinable with the formed vapor to form an aerosol. According to example implementations of the present disclosure, the formed vapor may be or include a condensing vapor and/or a non-condensing vapor that may be combinable with the air to respectively form a condensation aerosol, non-condensation aerosol, or a combination thereof.

In some examples, the vaporization elements 210, 212 may include mechanisms for respectively forming condensing and non-condensing vapors. In these examples, the consolidation of the two aerosol delivery mechanisms (e.g., condensation and non-condensation mechanisms) into a single aerosol delivery device may offer several benefits over traditional or modified systems that exclusively produce a condensation aerosol. The benefits may include a reduction in levels of glycerin and/or propylene glycol thermal degradation compounds (e.g., formaldehyde, acetaldehyde, glycidol, propylene oxide, and the like), customizable aerosol delivery profiles, mitigation of charring at a heater one of the elements and/or its supporting fluid transport element, and improved sensory experience as a result of the non-heated electromechanical production of a non-condensation aerosol vapor. In particular, the non-condensation aerosol vapor may require less energy at the heater to vaporize the components of the aerosol precursor composition deposited in comparison to the components of the aerosol precursor composition contained in a liquid transport element (e.g., a fibrous wick bundle). In which, the decrease in energy required at the heater may resultantly cause the lower levels of thermal degradation or decomposition compounds.

Accordingly, in some examples, the vaporization elements 210, 212 of FIG. 2 may respectively include a condensing vaporization element (e.g., a first element) and a non-condensing vaporization element (e.g., a second element). In some examples, the condensing and non-condensing vaporization elements may be removably coupled to the housing 106, and thus replaceable by a consumer, as needed. The condensing and non-condensing vaporization elements may be configured to activate and vaporize components of an aerosol precursor composition, and thereby form respectively a condensing vapor and non-condensing vapor. In response to a flow of air through at least a portion of the at least one housing, the condensing vapor or non-condensing vapor may be combinable with the air to form an aerosol. In these examples, it should be noted that although the aerosol delivery device may include both vaporization elements, the vaporization elements may be used either independently and/or interchangeably for forming only one of either the condensing vapor or non-condensing vapor during draw upon the aerosol delivery device for aerosol inhalation.

As previously indicated, in some example implementations, the reservoir 208 defined within the housing 106 may be a refillable reservoir for storing aerosol precursor composition. In these example implementations, the housing may also define a port 222 mateable with only a corresponding container of aerosol precursor composition for refilling the reservoir.

Also as previously indicated, the control valve 214 may be configured to control a flow of aerosol precursor composition from the reservoir to each of the vaporization elements 210, 212 (e.g., a condensing vaporization element and non-condensing vaporization element). In some examples, the reservoir 208 may provide aerosol precursor composition to both the vaporization elements via respective channels. The valve may control the flow of aerosol precursor composition from the reservoir such that the amount of aerosol precursor directed toward either element may be tuned, such as by a consumer. As such, an aerosol delivery profile (e.g., a controllable ratio of condensation to non-condensation aerosol being delivered) may thereby be customized. For example, the aerosol delivery profile may include the delivery of 100% condensation aerosol and 0% non-condensation or 50% condensation aerosol and 50% non-condensation aerosol.

In some example implementations in which the vaporization element 210 includes a condensing vaporization element, as suggested above, the condensing vaporization element may include a heater configured to activate and vaporize components of the aerosol precursor composition by a heating action. In some examples, the condensing vaporization element may also include a liquid transport element configured to transport aerosol precursor composition from the reservoir 208, and in these examples, the heater may be configured to activate and vaporize components of the aerosol precursor composition so transported by the liquid transport element.

Various examples of materials configured to produce heat when electrical current is applied therethrough may be employed to form the heater. The heater in these examples may be a resistive heating element such as a coil. Example materials from which the coil may be formed include Titanium (Ti), Platinum (Pt), Kanthal (FeCrAl), Nichrome, Molybdenum disilicide ($MoSi_2$), molybdenum silicide (MoSi), Molybdenum disilicide doped with Aluminum ($Mo(Si,Al)_2$), graphite and graphite-based materials (e.g., carbon-based foams and yarns) and ceramics (e.g., positive or negative temperature coefficient ceramics). The heater may comprise a wire structure defining a mesh, screen or lattice structure positioned about the liquid transport element. Example materials from which the wire mesh, screen, or lattice that may be formed of, or include titanium, platinum, silver, palladium, Kanthal (FeCrAl), Nichrome, Molybdenum disilicide ($MoSi_2$), molybdenum silicide (MoSi), Molybdenum disilicide doped with Aluminum ($Mo(Si,Al)_2$), Silver Palladium (Ag/Pd) conductive inks, graphite and graphite-based materials; and ceramic (e.g., a positive or negative temperature coefficient ceramic).

In some example implementations, in which the vaporization elements 210, 212 respectively include condensing and non-condensing vaporization elements, the non-condensing vaporization element (e.g., a second element) may be an electromechanical device configured to activate and vaporize components of an aerosol precursor composition by a mechanical action. Examples of a suitable electromechanical device may be or include a piezoelectric ultrasonic atomizer as described in U.S. Pat. No. 7,954,730 to Ng, filed May 2, 2005, which is incorporated herein by reference; or a piezoelectric ultrasonic transducer as described in U.S. Pat. No. 6,763,722 to Fjield et al., filed Jul. 13, 2001, which is incorporated herein by reference. In some examples, the heater of the condensing vaporization element (e.g., a first element) may be configured to activate and vaporize components of the aerosol precursor composition transported thereto by the liquid transport element and/or the electromechanical device. And in at least one instance, the heater may simultaneously vaporize components of the aerosol precursor composition transported thereto by both the liquid transport element and the electromechanical device for forming a combination of condensation and non-condensation aerosol.

For example, the non-condensing vaporization element (e.g., a second vaporization element 212) may be configured to form and direct a non-condensing vapor to the condensing vaporization element (e.g., a first vaporization element 210). In which, the condensing vaporization element may be configured to activate and vaporize components of the non-condensing vapor to thereby form a condensation aerosol. For example, the non-condensing vaporization element may produce an aerosol "mist" that can be further vaporized downstream by the first vaporization element (e.g., a heater) to turn the aerosol mist into an aerosol vapor or gas that subsequently condenses to form the condensation aerosol.

In a particular implementation, the non-condensing vaporization element 212 may be or include an electromechanical device configured to produce the non-condensation aerosol via piezoelectric ultrasonic oscillations, for example. Condensation aerosols have a substantially smaller average particle size than a "mist". In some examples implementations, the non-condensing vapor may include a particle-size distribution in which a substantial majority of the particles are less than 1 µm in diameter. The resulting condensation aerosol may similarly contain particles having a small particle-size distribution allowing the particles to be easily pulled through the mouthpiece 216.

In some example implementations, in which the vaporization elements 210, 212 respectively include condensing and non-condensing vaporization elements, the condensing vaporization element being configured to activate and vaporize components of the non-condensing vapor may include the condensing vaporization element being configured to activate simultaneously with the non-condensing vapor being directed to the condensing vaporization element. For example, the condensing vaporization element may include a heating module being activated in tandem or simultaneously, as the non-condensing vaporization element (e.g., electromechanical device) directs the non-condensing vapor to the condensing vaporization element. The condensing vaporization element may then vaporize the non-condensing vapor deposited on a surface of the heating. In alternative example implementations, the condensing vaporization element may be activated slightly before, slightly after the non-condensing vaporization element directs the non-condensing vapor (e.g., an aerosol mist) onto a surface of the condensing vaporization element.

As previously indicated, in some examples the vaporization elements 210, 212 may respectively include condensing and non-condensing vaporization elements, and the aerosol delivery device may produce both a condensing vapor using the condensing vaporization element (e.g., a traditional wick and coil configuration) and/or a non-condensing vapor using the non-condensing vaporization element (e.g., an alternative electromechanical fluid delivery and heating mechanism). Further examples of an alternative electromechanical fluid delivery and heating mechanisms are described in U.S. patent application Ser. No. 14/524,778 to Brammer et al., which is incorporated herein by reference.

FIGS. 3A and 3B more particularly illustrate condensing (e.g., a first element) and non-condensing (e.g., a second element) vaporization elements 210, 212, according to an example implementation of the present disclosure. As shown in FIGS. 3A and 3B, in some example implementations, the condensing and non-condensing vaporization elements may be positioned proximately parallel to one another. In these example implementations, the parallel configuration may promote optimal deposition of the non-condensation aerosol onto a surface of the condensing vaporization element (e.g., surface of a micro-heater). The distance between the condensing and non-condensing vaporization elements may range between one (1) millimeter and ten (10) centimeters inclusive. In these examples implementations, the flow of air through at least the portion of the at least one housing 106 may be transversely or longitudinally directed toward the non-condensing vapor based on a velocity thereof. After vaporization of the vapor directed and/or deposited onto the surface of the condensing vaporization element, the transverse and/or longitudinal airflow may direct the condensation aerosol around the condensing vaporization element and out of the mouthpiece 216.

In some other examples, the vaporization elements 210, 212 may include mechanisms for respectively modifying a vapor and forming a non-condensing vapor. Accordingly, in these examples, the vaporization elements 210, 212 of FIG. 2 may respectively include a vapor modification element (e.g., a first element) and a non-condensing vaporization element (e.g., a second element). In some examples, the vapor modification and non-condensing vaporization elements may be removably coupled to the housing 106, and thus replaceable by a consumer, as needed. The non-condensing vaporization elements may be configured to activate and vaporize components of an aerosol precursor composition, and thereby form a non-condensing vapor in which the non-condensing vapor is modified by the vapor modification element. In response to a flow of air through at least a portion of the at least one housing, the non-condensing vapor may be combinable with the air to form an aerosol.

In some example implementations, in which the vaporization elements 210, 212 respectively include vapor modification and non-condensing vaporization elements, the vapor modification element may include a drying tube configured to modify the non-condensing vapor by a moisture removal action. In particular, the drying tube may be configured to remove moisture from the non-condensing vapor formed by the non-condensing vaporization element, and thereby reduce a particle-size of the non-condensing vapor. In some examples, the vapor modification element may additionally and/or alternatively include a flavor modifier configured to modify the non-condensing vapor by a flavor injection action. In particular, the flavor modifier may be configured to inject volatile favors into the non-condensing vapor formed by the non-condensing vaporization element according to various means discussed hereinafter. Examples of suitable flavor modifiers may be or include thermal bubble jet printheads, a packed-bed of volatile flavors (e.g., a plurality of beads made from tobacco, menthol, and the like), or another suitable mechanism flavor injection mechanism not explicitly contemplated herein.

In these examples, the consolidation of such mechanisms (e.g., vapor modification and non-condensation mechanisms) into a single aerosol delivery device may offer several benefits. In instances in which the vapor modification element includes a drying tube, the benefits may include reducing the traditional particle-size of vapor formed by an electromechanical means (e.g., non-condensing vapor). In instances in which the vapor modification element includes a flavor modifier, the benefits may include injecting flavors into water-based solutions as electromechanical devices are more compatible with water-based solutions and traditional flavors may be hydrophobic. Flavor modifiers can be added subsequent to aerosol formation using various means (e.g., thermal bubble jet or elution from a packed bed). This may allow the primary aerosol precursor to be predominately water-based in composition.

In some example implementations, in which the vaporization elements 210, 212 respectively include vapor modification and non-condensing vaporization elements, the vapor modification element being configured to modify the non-condensing vapor may include the vapor modification element being configured to activate simultaneously with the non-condensing vapor being directed to the vapor modification element. For example, the non-condensing vapor may be directed toward and/or into the vapor modification element by the non-condensing vaporization element for modification thereby. In a specific example in which the vapor modification element is a drying tube, non-condensing vapor may be dispersed throughout the drying tube configured to thereby remove moisture from the vapor by pulling a water shell from the corresponding aerosol droplets, thus reducing the overall particle-size.

It should be noted that although some example implementations are discussed with respect to the vaporization elements 210, 212 respectively including a combination of condensing and non-condensing vaporization elements, or an alternative combination of vapor modification and non-condensing vaporization elements, the vaporization elements may include any combination of condensing, non-condensing, and/or vapor modification elements including one or more of a heater, electromechanical device, drying tube or flavor modifier. For example, in one implementation, the vaporization elements may include first, second, third and/or fourth vaporization elements. Further it should be noted that the vapor modification and non-condensing vaporization elements, may be positioned similarly to examples implementations discussed with respect to the condensing and non-condensing vaporization elements.

FIG. 4 illustrates various operations in a method 400 of controlling an aerosol delivery device according to an example implementation of the present disclosure. The aerosol delivery device may comprise at least one housing and a first and second element contained within the at least one housing. As shown in block 402, the method may include activating the first element and second element. At the first element and second element so activated, the method may also include vaporizing components of an aerosol precursor composition, and thereby forming respectively a condensing vapor and non-condensing vapor, as shown at block 404. The first element and second element may activate and vaporize components of the aerosol precursor composition in response to a flow of air through at least a portion of the at least one housing in which the condensing vapor or non-condensing vapor may be combinable with the air to form an aerosol.

FIG. 5 illustrates various operations in a method 500 of controlling an aerosol delivery device according to an example implementation of the present disclosure. The aerosol delivery device may comprise at least one housing and a first and second element contained within the at least one housing. As shown in block 502, the method may include activating the first element and second element. At the second element so activated, the method may also include vaporizing components of the aerosol precursor composition to thereby form a non-condensing vapor in response to a flow of air through at least a portion of the at least one housing, as shown at block 504. At the first element so activated, modifying the non-condensing vapor, in which the non-condensing vapor therefrom is combinable with the air to form an aerosol, as shown at block 506.

The foregoing description of use of the article(s) can be applied to the various example implementations described herein through minor modifications, which can be apparent to the person of skill in the art in light of the further disclosure provided herein. The above description of use, however, is not intended to limit the use of the article but is provided to comply with all necessary requirements of disclosure of the present disclosure. Any of the elements shown in the article(s) illustrated in FIGS. 1-4 or as otherwise described above may be included in an aerosol delivery device according to the present disclosure.

Many modifications and other implementations of the disclosure set forth herein will come to mind to one skilled in the art to which these disclosure pertain having the benefit of the teachings presented in the foregoing descriptions and the associated drawings. Therefore, it is to be understood that the disclosure are not to be limited to the specific implementations disclosed and that modifications and other implementations are intended to be included within the scope of the appended claims. Moreover, although the foregoing descriptions and the associated drawings describe example implementations in the context of certain example combinations of elements and/or functions, it should be appreciated that different combinations of elements and/or functions may be provided by alternative implementations without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

What is claimed is:

1. An aerosol delivery device comprising:
   at least one housing defining a reservoir for storing aerosol precursor composition; and
   a first element and second element contained within the at least one housing and configured to activate and vaporize components of the aerosol precursor composition, and thereby form respectively a condensing vapor and non-condensing vapor, in response to a flow of air through at least a portion of the at least one housing, at least one of the condensing vapor or non-condensing vapor being combinable with the air to form an aerosol, the first element being positioned separated and in parallel with the second element to enable deposition of the non-condensing vapor onto a surface of the first element.

2. The aerosol delivery device of claim 1, wherein the first element and second element are respectively a heater and electromechanical device configured to vaporize components of an aerosol precursor composition by respectively a heating action and mechanical action.

3. The aerosol delivery device of claim 1, wherein the first element and second element being contained within the at least one housing includes the first element and second element being removably coupled to the at least one housing.

4. The aerosol delivery device of claim 1 further comprising a control valve configured to control a flow of aerosol precursor composition from the reservoir to the first element and second element.

5. The aerosol delivery device of claim 1, wherein the reservoir is refillable, and the at least one housing further defines a port mateable with only a corresponding container of aerosol precursor composition for refilling the reservoir.

6. The aerosol delivery device of claim 1, wherein the first element includes a liquid transport element configured to transport aerosol precursor composition from the reservoir, and a heater configured to activate and vaporize components of the aerosol precursor composition so transported by the liquid transport element.

7. The aerosol delivery device of claim 1, wherein the second element being configured to form and direct the non-condensing vapor to the first element, and the first element being configured to activate and vaporize components of the non-condensing vapor to thereby form the condensing vapor.

8. The aerosol delivery device of claim 7, wherein a distance between the first element and second element is between one (1) millimeter and ten (10) centimeters inclusive.

9. The aerosol delivery device of claim 7, wherein the first element being configured to activate includes being configured to activate simultaneously with the non-condensing vapor being directed to the first element.

10. The aerosol delivery device of claim 7, wherein the flow of air through at least the portion of the at least one housing is transversely or longitudinally directed toward the non-condensing vapor based on a velocity thereof.

11. An aerosol delivery device comprising:
at least one housing defining a reservoir for storing aerosol precursor composition; and
a first element and second element contained within the at least one housing, the second element being configured to activate and vaporize components of the aerosol precursor composition to thereby form a non-condensing vapor in response to a flow of air through at least a portion of the at least one housing, and the first element being configured to modify the non-condensing vapor, the non-condensing vapor therefrom being combinable with the air to form an aerosol, the first element being positioned separated and in parallel with the second element.

12. The aerosol delivery device of claim 11, wherein the first element and second element are respectively a vapor modification element and electromechanical device, the electromechanical device being configured to vaporize components of an aerosol precursor composition by a mechanical action, and the vapor modification element being configured to modify the non-condensing vapor by a moisture removal action.

13. The aerosol delivery device of claim 11, wherein the first element and second element are respectively a vapor modification element and electromechanical device, the electromechanical device being configured to vaporize components of an aerosol precursor composition by a mechanical action, and the vapor modification element being configured to modify the non-condensing vapor by injecting a volatile flavor into the non-condensing vapor.

14. The aerosol delivery device of claim 11, wherein the first element is a vapor modification element includes at least one of a drying tube or flavor modifier respectively configured to modify the non-condensing vapor by a moisture removal action and flavor injection action.

15. The aerosol delivery device of claim 11 further comprising a third element, wherein in response to a flow of air through at least a portion of the at least one housing, the third element being configured to activate and vaporize components of the aerosol precursor composition to thereby form a condensing vapor, and the first element being further configured to modify the condensing vapor or non-condensing vapor, at least one of the condensing vapor or non-condensing vapor therefrom being combinable with the air to form an aerosol.

16. The aerosol delivery device of claim 15, wherein the second and third elements are respectively a electromechanical device and heater configured to vaporize components of an aerosol precursor composition by respectively a mechanical action and heating action, and the first element is a vapor modification element configured to modify the condensing or non-condensing vapor by injecting a volatile flavor into the condensing or non-condensing vapor.

* * * * *